United States Patent
Kharia et al.

(10) Patent No.: US 11,273,156 B2
(45) Date of Patent: Mar. 15, 2022

(54) STABLE CAPRAZINE FORMULATIONS FOR ORAL USE

(71) Applicants: Ankit Anand Kharia, Hyderabad (IN); Sunil Chowdary Koduri, Hyderabad (IN); Jaikishore Palepu, Hyderabad (IN); Nagaprasad Vishnubhotla, Hyderabad (IN); Sivakumaran Meenakshisunderam, Hyderabad (IN)

(72) Inventors: Ankit Anand Kharia, Hyderabad (IN); Sunil Chowdary Koduri, Hyderabad (IN); Jaikishore Palepu, Hyderabad (IN); Nagaprasad Vishnubhotla, Hyderabad (IN); Sivakumaran Meenakshisunderam, Hyderabad (IN)

(73) Assignee: Aurobindo Pharma Ltd, Hyderabad (IN)

(*) Notice: Subject to any disclaimer, the term of this patent is extended or adjusted under 35 U.S.C. 154(b) by 150 days.

(21) Appl. No.: 16/687,502

(22) Filed: Nov. 18, 2019

(65) Prior Publication Data

US 2020/0155546 A1    May 21, 2020

(30) Foreign Application Priority Data

Nov. 20, 2018 (IN) .............................. 201841043642

(51) Int. Cl.
*A61K 31/495* (2006.01)
*A61K 9/00* (2006.01)

(52) U.S. Cl.
CPC .......... *A61K 31/495* (2013.01); *A61K 9/0053* (2013.01)

(58) Field of Classification Search
CPC .................................................... A61K 31/495
See application file for complete search history.

(56) References Cited

U.S. PATENT DOCUMENTS

2011/0059980 A1* 3/2011 Oobayashi ........... A61K 31/495
514/252.12

FOREIGN PATENT DOCUMENTS

WO    WO 2017178999    * 10/2017

* cited by examiner

*Primary Examiner* — Rei Tsang Shiao
(74) *Attorney, Agent, or Firm* — Jay R Akhave; PatentScience LLC

(57) ABSTRACT

The present invention relates to stabilized pharmaceutical formulations comprising therapeutically effective amount of Cariprazine premix/solid dispersion, or its pharmaceutically acceptable salts, esters, hydrates and solvates thereof, at least one diluent which is not having low water activity and optionally one or more excipients selected from lubricant, disintegrant and buffering agent or combinations thereof. The present invention further relates to process for preparation and method of using such stable formulations comprising Cariprazine.

9 Claims, No Drawings

STABLE CARIPRAZINE FORMULATIONS FOR ORAL USE

CROSS REFERENCE TO RELATED APPLICATIONS

This application claims priority from an Indian Patent Application IN 201841043642 filed on Nov. 20, 2018

FIELD OF THE INVENTION

The present invention relates to stabilized pharmaceutical formulations comprising a biologically active dopamine receptor ligand i.e. Cariprazine, wherein the said stable formulations preferably release the drug rapidly and exhibits desired bioavailability. Particularly the present invention relates to stabilized pharmaceutical formulations comprising a premix/solid dispersion of Cariprazine, or its pharmaceutically acceptable salts, esters, hydrates and solvates thereof, process of preparation and method of using the same.

BACKGROUND OF THE INVENTION

Cariprazine, is an orally active atypical antipsychotic. It acts as a potent dopamine D3 and D2 receptor partial agonist, which preferentially binds to the D3 receptor. Cariprazine also has partial agonist activity at serotonin 5-HT1A receptors. The chemical name is trans-N-{4-[2-[4-(2,3-dichlorophenyl)piperazine-1-yl]ethyl]cyclohexyl}-N', N'-dimethylurea. Cariprazine is structurally represented as:

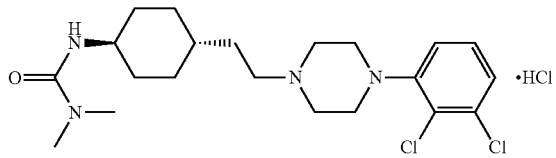 [SMILES: CN(C)C(=O)N[C@H]1CC[C@H](CCN2CCN(c3cccc(Cl)c3Cl)CC2)CC1 ; Cl]

Cariprazine is used to treat schizophrenia. Cariprazine is also used to treat people with bipolar I disorder when they are experiencing episodes of mania or mixed episodes. It is also potentially useful as an add-on therapy in major depressive disorder. It works by changing the activity of certain natural substances in the brain. It is also known as a second-generation antipsychotic (SGA) or atypical antipsychotic. Currently Cariprazine (1.5 mg, 3 mg, 4.5 mg, and 6 mg) is marketed under brand name "VRAYLAR®" in the United States by Allergan Sales LLC/Forest Laboratories and is supplied as capsules for oral administration.

Cariprazine undergoes hydrolytic degradation in the presence of excipients having high water activity and degradation of the active ingredient mainly depends upon the amount of free water released from the excipient, which is responsible for hydrolytic degradation. The degradation product i.e. trans-4-[2-[4-(2,3-dichlorophenyl)-piperazin-1-yl]-ethyl]-cyclohexyl-amine dihydrochloride (De-BOC) is formed by the hydrolytic cleavage of the amide bond of Cariprazine, when formulated with commonly used excipients (e.g., anhydrous dicalcium phosphate, and microcrystalline cellulose). Further it is known that the stability of Cariprazine depends on the solid state microenvironmental pH of the formulation, wherein rising of pH enhances stability of Cariprazine by reducing ionization of the weakly basic drug and thereby inhibiting hydrolysis.

Considering the stability of Cariprazine and its bioavailability, there is a need for development of pharmaceutical formulations of Cariprazine with desired bioavailability and stability at different storage conditions. The formation of a degradation product such as De-BOC in a pharmaceutical formulation is detrimental to activity. Moreover, if the amount of degradation product exceeds FDA guidelines, additional safety and toxicology testing must be undertaken. Thus the goal of the present invention is to formulate an immediate release Cariprazine solid formulation with desired bioavailability and good stability.

U.S. Pat. No. 7,737,142 discloses the Cariprazine product and other related products. Several attempts have been made in the prior art to provide stable oral formulations of Cariprazine. U.S. Pat. No. 7,943,621 discloses Trans isomer of Cariprazine and its crystalline forms, it also discloses formulations of Cariprazine. U.S. Pat. Nos. 9,056,845 & 9,056,846 discloses formulations of Cariprazine with an excipient having low water activity selected from the group consisting of pregelatinized starch, mannitol, anhydrous calcium hydrogen phosphate, and mixtures thereof for treating a condition selected from the group of schizophrenia, bipolar disorder, acute mania, and depression, wherein the formulation has a pH in the range of about 9.0 to about 12.0. Further the above said patents discloses that these formulations show between about 0.1% and about 0.5% of De-BOC or a pharmaceutically acceptable salt thereof; as well as provides an in vivo plasma profile comprising a mean Cmax of less than about 26.3 ng/mL, a mean AUC0-∞ of more than about 2 ng·hr/mL and a mean Tmax of about 3 or more hours, wherein the formulation has a dissolution rate of more than about 80% within about the first 60 minutes following administration of the formulation. Furthermore the patents US'845 & US'846 also states that, the preparation of stable and bioavailable dosage forms containing Cariprazine is not straightforward. The said patents also disclose the following: "the use of low-moisture grade microcrystalline cellulose (e.g., Avicel PH 112), moisture absorbing/adsorbing agents (e.g., magnesium oxide) or chelating agents (e.g., ethylenediamaintetraacetic acid "EDTA") does not provide formulations with enhanced stability toward hydrolytic degradation product formation." U. S. Publication No. US20110059980A1 discloses a solid preparation for oral administration which comprises lactose as a main excipient and comprises Cariprazine hydrochloride. PCT Publication No. WO2017178999A1 discloses a granule formulation of Cariprazine for oral administration, wherein said granule formulation uses a diluent that contains lactose, crystalline cellulose or starch, with the percentage content of the total quantity of diluent being 70 to 100 wt % of lactose, 0 to 25 wt % of crystalline cellulose, and 0 to 5 wt % of starch. U.S. Pat. No. 7,829,569 discloses a crystalline form of trans-1{4-[2-[4-(2,3 dichlorophenyl)-piperazin-1-yl]-ethyl]-cyclohexyl}-3,3-dimethyl-ureahydrochloride (Form III) having a X-ray powder diffraction pattern comprising characteristic peaks at about 4.1, about 12.3, about 16.5, and about 17.4±0.2 degrees 2θ.

The aforementioned prior art formulations of Cariprazine are stable for a less period or undergo premature degradation upon different storage conditions. Further the currently marketed Cariprazine oral formulation with pregelatinized starch exhibits improved stability of Cariprazine along with desired bioavailability, but still has impurities including 0.1% to about 0.5% of De-BOC impurity (according to US'845 patent). Hence, there still exists a need for developing the stable, bioavailable and immediate release Cariprazine formulations that are commercially viable and easy to manufacture. Therefore, the inventors of the present invention have developed pharmaceutical formulations comprising a premix/solid dispersion of Cariprazine and other excipients which are commercially viable and easy to manufacture, wherein the said formulations preferably release the drug rapidly, exhibits the desired bioavailabity and demonstrates good stability profiles. The excipients and the process of preparation used in the present invention stabilizes the formulation, provides rapid drug release, improves bioavailability and alleviates the limitations in the art by providing commercially viable Cariprazine oral preparations with less degradation.

SUMMARY OF INVENTION

The present invention relates to stable solid oral formulations comprising therapeutically effective amount of Cariprazine premix/solid dispersion, at least one diluent which is not having low water activity and optionally one or more excipients selected from lubricant, disintegrant and buffering agent or combinations thereof. The said formulation provides good stable, bioavailable and immediate release formulations. The present invention teaches away from US'845 and US'846 patents which require using of specialized excipients that have low water activity for preparing Cariprazine formulations that rapidly release's the drug, exhibits the desired bioavailabity and demonstrates good stability profiles. Moreover the present inventors have now surprisingly found that, well-known routine pharmaceutical excipients in the art and few conventional methods are capable of stabilizing Cariprazine formulations along with providing desired bioavailability and rapid release, without using of specialized excipients that have low water activity and without raising the solid state microenvironmental pH of the formulation.

In an aspect of the invention, the said stable, bioavailable and immediate release oral formulations comprise therapeutically effective amount of Cariprazine premix/solid dispersion and at least one diluent selected form the group consisting of microcrystalline cellulose, maltodextrin, sucrose, xylitol, lactose, dextrose, sorbitol, dextrates, lactitol, kaolin, starlac, dibasic calcium phosphate, tribasic calcium phosphate, calcium carbonate, calcium sulfate, magnesium carbonate, magnesium oxide or a combination thereof.

The invention further provides that, Cariprazine premix/solid dispersion comprises Cariprazine in substantially amorphous form which is dispersed in a pharmaceutically acceptable polymer/carrier.

In an aspect of the invention, the said stable and bioavailable Cariprazine formulation consists of hydrolysis degradation product in an amount that is less than about 0.5% w/w after exposure to accelerated storage conditions for about 6 months.

In an aspect of the invention, the said stable Cariprazine formulation upon a single dose administration of the formulation provides an in vivo plasma profile that is bioequivalent to currently marketed Cariprazine Capsules (VRAYLAR®; 1.5 mg, 3 mg, 4.5 mg, and 6 mg).

In an aspect, the present invention provides process for the preparation of stable oral pharmaceutical formulations, wherein the process comprises of the following steps: (i) preparing the premix/solid dispersion of Cariprazine (ii) co-sifting Cariprazine with excipients except lubricant (iii) lubricating step (ii) blend with lubricant. (iv) formulating the blend of step (iii) into a suitable dosage form. The invention further provides a process of preparation of the said premix/solid dispersion of Cariprazine which comprises: i) providing a solution of Cariprazine in a solvent; ii) adding a pharmaceutically acceptable polymer/carrier; iii) isolating amorphous premix/solid dispersion of Cariprazine.

In another aspect, the present invention also relates to a method of using such formulations for treatment of patients with schizophrenia, bipolar disorder, acute mania, and depression.

Other features and advantages of the invention will be apparent from the following detailed description, and from the claims.

DETAILED DESCRIPTION OF THE INVENTION

Within the scope of the description of the invention, Cariprazine and any of its addition salts are referred to as "Cariprazine". Also, unless otherwise stated, the terms "active ingredient" and "active substance" refer to Cariprazine and any of its pharmaceutically acceptable salts or esters, hydrates and solvates thereof. Preferably Cariprazine is in the form of a pharmaceutically acceptable acid addition salt, more preferably, in the form of its hydrochloride salt. The term 'pharmaceutically acceptable' as used herein, refers to materials that are suitable for use in contact with the tissues of humans and lower animals without undue toxicity, irritation, allergic response, and the like, in keeping with a reasonable benefit-risk ratio, and effective for their intended use. The effective therapeutic amount of the active principle is advantageously such that the unit content of Cariprazine and its pharmaceutically acceptable salts is from 1 mg to 15 mg. The term 'stable' refers to formulations that substantially retain the label amount of the therapeutically active ingredient during storage for commercially relevant times, and the drug-related impurity contents in the formulations remain within acceptable limits. Further, the term 'stable' also optionally refers to formulations that contain polymorphically stable active ingredient. The phrase "substantially amorphous form" of Cariprazine unless otherwise specified is to be understood as a substance free of other polymorphic and/or pseudopolymorphic forms at amounts detectable with typical analytical methods such as X-ray powder diffraction and/or solid state infrared absorption, i.e. containing less than 10% of other polymorphic and/or pseudopolymorphic forms. The term "solid dispersion" refers to the dispersion of Cariprazine in a solid state polymer matrix prepared by a variety of methods, including spray drying, the melting (fusion), solvent, or the melting-solvent method. As used herein, the term "premix" refers to solid mixtures of Cariprazine and at least one pharmaceutical excipient/carrier, wherein individual particles of the components cannot be distinguished using techniques such as optical microscopy. The premixes or solid dispersions of the present invention may provide multiple benefits in preparing formulations of Cariprazine, for example, improved processability, increased stability of the pharmaceutical formulation or API, or improved pharmacokinetic properties of the pharmaceutical formulation. The term "bioequivalent" means the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. In practice, two products are considered bioequivalent if the 90% confidence interval of the Cmax, AUC, or, optionally, Tmax is within the range of 80.00% to 125.00%).

In embodiments, the pharmaceutical formulation provided herein comprises excipients which act as diluents.

Certain non-limiting examples of diluents include microcrystalline cellulose, maltodextrin, sucrose, xylitol, lactose, dextrose, sorbitol, dextrates, lactitol, kaolin, starlac, dibasic calcium phosphate, tribasic calcium phosphate, calcium carbonate, calcium sulfate, magnesium carbonate and magnesium oxide, starch and modified starches. Preferably the diluent is selected from silicified microcrystalline cellulose, maltodextrin, sucrose, xylitol, microcrystalline cellulose (Avicel-PH-102; Avicel-PH-112), lactose and combinations thereof. In embodiments, the pharmaceutical formulation provided herein comprises diluents in the range of about 25% w/w to about 99% w/w of the formulation. Preferably the pharmaceutical formulations provided herein comprises diluents in the range of about 60% w/w to about 97% w/w of the formulation. In embodiments, the premix/solid dispersion provided herein comprises polymer/carrier. Certain non-limiting examples of the polymers/carriers include copovidone, povidone, hypromellose, hydroxylpropyl cellulose, polyvinyl caproiactam-polyvinyl acetate-polyethylene glycol and combinations thereof. Preferably the polymer/carrier is selected from copovidone & povidone. In embodiments, the said polymer/carrier may also be added as a part of dry mix in order to maintain same % w/w of copovidone to the total fill weight of dosage form across the strengths. In embodiments, the premix/solid dispersion provided herein comprises the ratio of Cariprazine to polymers/carriers in a range of 1:10 to 10:1. Preferably the premix/solid dispersion provided herein comprises the ratio of Cariprazine to polymers/carriers in a range of 1:1.

In embodiments, the pharmaceutical formulation provided herein includes optionally one or more excipients selected from lubricant, glidant, disintegrant, binder and buffering agent or combinations thereof. Disintegrants according to the present invention are selected from, but not limited to, cellulose and its derivatives including low-substituted hydroxypropyl cellulose; cross-linked polyvinylpyrrolidone; polyvinylpyrrolidone; cross-linked sodium carboxymethylcellulose, sodium carboxymethylcellulose, microcrystalline cellulose; sodium starch glycolate; ion-exchange resins; starch and modified starches; formalin-casein; used either alone or combinations thereof. Lubricants and glidants aids in the processing of powder materials. Exemplary lubricants are selected from, but not limited to, calcium stearate, magnesium stearate, glycerol behenate, mineral oil, polyethylene glycol, sodium stearyl fumarate, stearic acid, talc, vegetable oil, and zinc stearate, used either alone or combinations thereof. Exemplary glidants include, but not limited to, talc, silicon dioxide, cornstarch and the like used either alone or in combination thereof. Binders hold the ingredients in the formulation together. Exemplary binders are selected from, but not limited to, cellulose and its derivatives including, ethyl cellulose, hydroxypropyl cellulose, hydroxypropyl methylcellulose, methylcellulose and hydroxyethyl cellulose, carboxymethyl cellulose; gelatin, liquid glucose; starch and its derivatives; hydrocolloids; sugars; polyvinyl pyrrolidone, sodium alginate, acacia, alginic acid, tragacanth, used either alone or combinations comprising one or more of the foregoing binders. Suitable buffering agents include, for example, organic compounds (e.g., triethylamine, arginine, diethanolamine, and meglumine), carbonates (e.g., sodium carbonate, lithium carbonate, potassium carbonate, magnesium carbonate) and bicarbonates (e.g., sodium bicarbonate, lithium bicarbonate, potassium bicarbonate, magnesium bicarbonate). More preferably sodium carbonate is used as buffering agent to improve the stability of active ingredient to obtain a stable Cariprazine formulation.

In one of the embodiments, measure of the chemical stability of Cariprazine is the amount of Cariprazine present in the Cariprazine formulations relative to the amount of structurally similar compounds including De-BOC Impurity DiDesmethyl Impurity, Desmethyl Impurity, Cariprazine dimer, and other unspecified Impurities. The amount of Cariprazine relative to the amount of these structurally similar compounds can be measured by high performance liquid chromatography (HPLC). The purity of Cariprazine and amounts of structurally similar compounds can be determined from peak areas obtained from HPLC to provide a measure of Cariprazine chemical stability. As used herein, unless otherwise defined, the term "accelerated storage conditions" refers to storage of Cariprazine at about 40° C. at about 75% relative humidity. In particular, the formulations of the present invention were stored under accelerated storage conditions for a period of at least 6 months, which then typically allows to predict or extrapolate corresponding stability data where the formulations are stored at room temperature in long-term conditions.

In embodiments, the formulation provided herein may also include other pharmaceutically acceptable excipient(s) selected from a group, comprising fillers, compression aids, colors, sweeteners, preservatives, surfactants, suspending agents, dispersing agents, film formers, flavors, printing inks, used either alone or in combination thereof. It must be appreciated that the pharmaceutical formulations of the present invention can include all the dosage forms known to a person skilled in art, viz. oral formulations such as single unit dosage forms in the form of tablets, minitablets filled in capsules and the like; beads, pellets presented in a sachet, capsule or tablets capsules such as soft and hard gelatin; lozenges or sachets; granulates, microparticles, multiparticulates, powder and the like. In the present invention, the preferred solid oral dosage forms are capsules. Capsules can be formulated as hard gelatin capsules or soft gelatin capsule. Hard gelatin capsules are mostly preferred in the present invention. Preferred Cariprazine capsule dosage forms having rapid drug release, good bioavailability and stability are made by combining Cariprazine with the pharmaceutically acceptable excipients selected from povidone, copovidone, silicified (Prosolv SMCC 90), maltodextrin (Glucidex IT 12), sucrose (60/200), xylitol (Xylisorb 300), microcrystalline cellulose (Avicel-PH-112), microcrystalline cellulose (Avicel-PH-102), lactose monohydrate USNF (Super Tab 11SD), croscarmellose sodium (AC-Di-Sol SD 711), sodium carbonate, magnesium stearate and combinations thereof.

In embodiments, the preparation of Cariprazine premix/solid dispersion provided herein includes solvent selected from water, ethanol, methanol propanol, isopropanol, butanol, acetone, methyl ethyl ketone, methyl isobutyl ketone. ethyl acetate, Diethyl carbonate, methyl acetate, isobutyl acetate, diethyl ether, diisopropyl ether, 1,4-dioxane, methyl tert-butyl ether, tetrahydrofuran, methyltetrahydrofuran, methylene chloride, Carbon tetrachloride, chloroform, chloro benzene, benzcne, toluene, hexane, cyclohexane, pentane, xylene, acetonitrile, dimethylforniarnide, dimethylsulfoxide or mixture thereof. In embodiments, the preparation of Cariprazine premix/solid dispersion provided herein includes isolation step which can be carried out by spray drying, evaporation, distillation, oven drying, tray drying, rota-vapor technique, freeze drying, fluid bed drying, flash drying, agitated thin film drying or melt extrusion method.

In embodiments, the present invention relates to a stable and bioavailable cariprazine formulation, wherein the said formulation consists of the amount of hydrolysis degradation product is less than about 1% w/w after exposure to accelerated storage conditions for about 6 months. Preferably the formulations of the present invention exhibits less than about 0.5% of "De-BOC impurity" after exposure to accelerated storage conditions for about 6 months. In embodiments, the present invention relates to a stable Cariprazine formulations containing from about 0.05 mg to about 15 mg Cariprazine wherein a single dose administration of the formulation provides an in vivo plasma profile that is bioequivalent to currently marketed Cariprazine Capsules (VRAYLAR®; 1.5 mg, 3 mg, 4.5 mg, and 6 mg).

In embodiments, the formulation provided herein can be prepared by the following process: i) take solvent into a flask (ii) charge Cariprazine hydrochloride followed by polymer/carrier into reaction mass (iii) stir the reaction mass and filter (iv) pass the solution into spray drier at appropriate temperature with 10 mL per minute flow rate. (v) collect the compound and dry to get the Cariprazine premix/solid dispersion. (vi) co-sift Cariprazine with excipients through sieve and mix for appropriate time in blender. (vii) lubricate the blend with lubricant in blender (viii) fill the blend into capsules or compress the blend to form a tablet. In embodiments, the formulation may optionally involve addition of polymer/carrier apart from the Cariprazine premix/solid dispersion.

In other embodiments, the formulation provided herein can be prepared by the following process (i) sift or co-sift diluent and the optional polymer/carrier (added as a part of dry mix) through 250 μm sieve. (ii) load materials of step (i) in blender and blend for 2 minutes and unload the material in to in-process containers. (iii) weigh step (ii) material about equal quantity of Cariprazine Hydrochloride premix and spread over the 250 μm sieve. (iv) spread the dispensed Cariprazine Hydrochloride premix over step (iii). (v) rinse the poly bag using step (ii) material about 2 times the quantity of Cariprazine Hydrochloride premix. (vi) weigh step (ii) material about equal quantity of Cariprazine Hydrochloride premix and spread over step (iv) along with poly bag rinsed material of step (v). (vii) sift material on 250 μm sieve after step (vi) and resift the same through 250 μm sieve. (viii) sift together step (viii) with about equal or remaining quantity (if remaining quantity is less than equal) of step (ii) material through 250 μm sieve and resift the same 250 μm sieve and continue the same procedure till entire step (ii) material quantity is consumed. (ix) sift the Lubricant through 250 μm sieve and collect separately. (x) load materials of step (vii) in blender and blend for 15 minutes. (xi) load sifted lubricant of step no. (ix) to step no (x) and blend for 5 minutes. (xii) unload the lubricated blend in to in-process containers. (xiii) fill the blend in empty hard gelatin capsule shells using the following parameters.

Although methods and materials similar or equivalent to those described herein can be used in the practice or testing of the present invention, suitable methods and materials are described below. The following examples are intended to serve as illustrations of the present invention and not intended to be limiting in any manner.

EXAMPLES

| INGREDIENTS | Strengths | | | |
|---|---|---|---|---|
| | 1.5 mg | 3 mg | 4.5 mg | 6 mg |
| | % w/w | | | |
| Example 1 | | | | |
| Cariprazine HCl-Copovidone Premix (1:1 w/w) | 2.96 | 5.92 | 8.88 | 11.84 |
| Copovidone USNF (Plasdone S-630) | 4.44 | 2.96 | 1.48 | 0 |
| Microcrystalline Cellulose USNF (Avicel-PH-112) | 91.60 | 90.12 | 88.64 | 87.16 |
| Magnesium Stearate (Ligamed) | 1.00 | 1.00 | 1.00 | 1.00 |
| Example 2 | | | | |
| Cariprazine HCl-Copovidone Premix (1:1 w/w) | 3.74 | 7.49 | 11.23 | 13.71 |
| Copovidone USNF (Plasdone S-630) | 4.98 | 3.11 | 1.24 | 0.00 |
| Microcrystalline Cellulose USNF (Avicel-PH-112) | 90.28 | 88.41 | 86.54 | 85.29 |
| Magnesium Stearate (Ligamed) | 1.00 | 1.00 | 1.00 | 1.00 |
| Example 3 | | | | |
| Cariprazine HCl-Copovidone Premix (1:1 w/w) | 5.92 | 5.92 | 5.92 | 5.92 |
| Sucrose USNF (60/200) | 93.01 | 93.01 | 93.01 | 93.01 |
| Magnesium Stearate (Ligamed) | 1.07 | 1.07 | 1.07 | 1.07 |
| Example 4 | | | | |
| Cariprazine HCl-Copovidone Premix (1:1 w/w) | 7.24 | 7.24 | 7.24 | 7.24 |
| Microcrystalline Cellulose USNF (Avicel-PH-112) | 45.88 | 45.88 | 45.88 | 45.88 |
| Sucrose USNF (60/200) | 45.88 | 45.88 | 45.88 | 45.88 |
| Magnesium Stearate (Ligamed) | 1.00 | 1.00 | 1.00 | 1.00 |
| Example 5 | | | | |
| Cariprazine HCl-Copovidone Premix (1:1 w/w) | 7.24 | 7.24 | 7.24 | 7.24 |
| Maltodextrin (GlucidexIT 12) | 26.05 | 26.05 | 26.05 | 26.05 |
| Sucrose USNF (60/200) | 65.71 | 65.71 | 65.71 | 65.71 |
| Magnesium Stearate (Ligamed) | 1.00 | 1.00 | 1.00 | 1.00 |
| Example 6: | | | | |
| Cariprazine HCl-Copovidone Premix (1:1 w/w) | 3.43 | 6.85 | 10.28 | 13.71 |
| Silicified MCC USNF (Prosolv SMCC 90) | 95.57 | 92.15 | 88.72 | 85.29 |
| Magnesium Stearate | 1.00 | 1.00 | 1.00 | 1.00 |
| Example 7 | | | | |
| Cariprazine HCl-Copovidone Premix (1:1 w/w) | 2.41 | 4.82 | 7.24 | 9.65 |
| Maltodextrin USNF (Glucidex IT 12) | 96.59 | 94.18 | 91.76 | 89.35 |
| Magnesium Stearate | 1.00 | 1.00 | 1.00 | 1.00 |
| Example 8 | | | | |
| Cariprazine HCl-Copovidone Premix (1:1 w/w) | 5.92 | 5.92 | 5.92 | 5.92 |
| Xylitol USNF (Xylisorb 300) | 93.08 | 93.08 | 93.08 | 93.08 |
| Magnesium Stearate | 1.00 | 1.00 | 1.00 | 1.00 |
| Example 9 | | | | |
| Cariprazine HCl-Copovidone Premix (1:1 w/w) | 5.54 | 5.54 | 5.54 | 5.54 |
| Sucrose USNF (60/200) | 78.46 | 78.46 | 78.46 | 78.46 |
| Croscarmellose Sodium (AC-Di-Sol SD 711) | 15.00 | 15.00 | 15.00 | 15.00 |
| Magnesium Stearate | 1.00 | 1.00 | 1.00 | 1.00 |

-continued

| Example 10 | | | | |
|---|---|---|---|---|
| Cariprazine HCl-Copovidone Premix (1:1 w/w) | 5.54 | 5.54 | 5.54 | 5.54 |
| Sucrose USNF (60/200) | 88.46 | 88.46 | 88.46 | 88.46 |
| Sodium Carbonate | 5.00 | 5.00 | 5.00 | 5.00 |
| Magnesium Stearate | 1.00 | 1.00 | 1.00 | 1.00 |
| Example 11 | | | | |
| Cariprazine HCl-Copovidone Premix (1:1 w/w) | 3.43 | 6.85 | 10.28 | 13.71 |
| Microcrystalline Cellulose USNF (Avicel-PH-102) | 95.57 | 92.15 | 88.72 | 85.29 |
| Magnesium Stearate | 1.00 | 1.00 | 1.00 | 1.00 |
| Example 12 | | | | |
| Cariprazine HCl-Copovidone Premix (1:1 w/w) | 6.85 | 6.85 | 6.85 | 6.85 |
| Lactose Monohydrate USNF (Super Tab 11SD) | 92.15 | 92.15 | 92.15 | 92.15 |
| Magnesium Stearate | 1.00 | 1.00 | 1.00 | 1.00 |

| INGREDIENTS | Strengths | | |
|---|---|---|---|
| | 1.5 mg | 3 mg | 6 mg |
| | % w/w | | |
| Example 13 | | | |
| Cariprazine HCl-Copovidone Premix (1:1 w/w) | 1.00 to 9.00 | 1.00 to 9.00 | 2.00 to 15.00 |
| Copovidone USNF (Plasdone S-630) | 0 to 7.0 | 0 to 6.0 | 0 to 5.00 |
| Microcrystalline Cellulose USNF (Avicel-PH-112) | 84.00 to 97.00 | 84.00 to 97.00 | 84.00 to 97.00 |
| Magnesium Stearate (Ligamed) | 1.00 to 3.00 | 1.00 to 3.00 | 1.00 to 3.00 |

Stability of Cariprazine Capsules was evaluated at different storage conditions by various parameters such as assay and impurities including major degradants i.e. De-BOC Impurity, DiDesmethyl Impurity, Desmethyl Impurity, and Cariprazine dimer. Further dissolution rate was determined by HPLC. Accelerated stability data and dissolution data is available for 3 mg and 6 mg strengths (prepared according to Example 13 of the present invention), for a storage period of at least 6 months at 40° C./75% Relative Humidity. The below Tables 1, 2, 3 and 4 shows the said stability data.

Accelerated Stability Data of Cariprazine Capsules 3 mg

TABLE 1

| Assay by HPLC | | | |
|---|---|---|---|
| Parameters | Initial | 3 Months | 6 Months |
| Amount of Cariprazine in each capsule | 2.923 (mg) | 2.945 (mg) | 2.945 (mg) |
| % Labelled amount | 97.4% | 98.2% | 98.2% |

TABLE 2

| Individual Specified Degradation products and Dissolution by HPLC | | | |
|---|---|---|---|
| Parameters | Initial (% w/w) | 3 Months (% w/w) | 6 Months (% w/w) |
| De-BOC Impurity | Below LOD (LOD: 0.026) | 0.216 | 0.393 |
| DiDesmethyl Impurity | Below LOD (LOD: 0.020) | Below LOQ (LOQ: 0.060) | Below LOQ (LOQ: 0.060) |

TABLE 2-continued

| Individual Specified Degradation products and Dissolution by HPLC | | | |
|---|---|---|---|
| Parameters | Initial (% w/w) | 3 Months (% w/w) | 6 Months (% w/w) |
| Desmethyl Impurity | Below LOD (LOD: 0.020) | Below LOQ (LOQ: 0.060) | 0.075 |
| Cariprazine dimer | 0.096 | 0.274 | 0.515 |
| Unspecified Impurities | 0.05 | Not Detected | 0.06 |
| Total Impurities | 0.146 | 0.49 | 1.043 |
| Dissolution (Percentage of the labelled amount base dissolved in 30 mins) | Min: 94.3 Max: 98.8 Avg: 96.6 | Min: 95.7 Max: 98.1 Avg: 96.5 | Min: 95.1 Max: 97.7 Avg: 96.3 |

Accelerated Stability Data of Cariprazine Capsules 6 mg

Table 3

| Assay by HPLC | | | |
|---|---|---|---|
| Parameters | Initial | 3 Months | 6 Months |
| Amount of Cariprazine in each capsule | 6.155 (mg) | 6.130 (mg) | 6.117 (mg) |
| % Labelled amount | 102.6% | 102.2% | 102.0% |

Table 4

| Individual Specified Degradation products and Dissolution by HPLC | | | |
|---|---|---|---|
| Parameters | Initial (% w/w) | 3 Months (% w/w) | 6 Months (% w/w) |
| De-BOC Impurity | Below LOD (LOD: 0.026) | 0.282 | 0.467 |
| DiDesmethyl Impurity | Below LOD (LOD: 0.020) | Below LOD (LOD: 0.020) | Below LOD (LOD: 0.020) |
| Desmethyl Impurity | Below LOD (LOD: 0.020) | Below LOD (LOD: 0.020) | Below LOD (LOD: 0.020) |
| Cariprazine dimer | 0.079 | 0.152 | 0.265 |
| Unspecified Impurities | Not Detected | Not Detected | Not Detected |
| Total Impurities | 0.079 | 0.434 | 0.732 |
| Dissolution (Percentage of the labelled amount base dissolved in 30 mins) | Min: 99.6 Max: 102.4 Avg: 101.0 | Min: 96.8 Max: 102.6 Avg: 100.2 | Min: 97.8 Max: 103.5 Avg: 100.3 |

Comparative bioavailability data is available for the marketed product (VRAYLAR®) and product prepared according to Example 13 (6 mg strength) of the present invention. The study was conducted on 39 patients in fasting condition, wherein the study was a multicentre open-label randomized, two-treatment, two-sequence, two-period, cross-over, multidose, steady state, clinical bioequivalence study. The below Table 5 shows the said comparative bioavailability data.

Table 5

| Summary of Bioavailability studies | | | |
|---|---|---|---|
| Mean Parameters for Cariprazine | | Cariprazine Capsules 6 mg (Example 13) | Cariprazine Capsules 6 mg (VRAYLAR®) |
| $C_{max}$ | Mean ± SD | 25.6844 ± 8.80192 ng/ml | 25.6752 ± 7.72897 ng/ml |
| | CV | 34.3% | 30.1% |
| $C_{min}$ | Mean ± SD | 9.6707 ± 5.49537 (ng/ml) | 8.9547 ± 3.93016 ng/ml |
| | CV | 56.8% | 43.9% |
| $T_{max}$ | Median | 2.50 hr | 2.50 hr |
| | Range | 1.00-5.00 | 1.00-5.00 |

Table 5-continued

Summary of Bioavailability studies

| Mean Parameters for Cariprazine | | Cariprazine Capsules 6 mg (Example 13) | Cariprazine Capsules 6 mg (VRAYLAR®) |
|---|---|---|---|
| $AUC_{0-t}$ | Mean ± SD | 357.1293 ± 160.72389 hr · ng/ml | 338.4193 ± 112.02138 hr · ng/ml |
| | CV | 45.0% | 33.1% |
| $C_{avg}$ | Mean ± SD | 14.8804 ± 6.69683 ng/ml | 14.1009 ± 4.66758 ng/ml |
| | CV | 45.0% | 33.1% |
| Fluctuation | Mean ± SD | 116.8488 ± 37.97538% | 124.4003 ± 39.83129 |
| | CV | 32.5% | 32.0% |
| Swing | Mean ± SD | 1.9858 ± 0.92589 | 2.1469 ± 1.02559 |
| | CV | 46.6% | 47.8% |

The above data suggests that Cariprazine formulation comprising Cariprazine HCl-copovidone premix (1:1 w/w), microcrystalline cellulose USNF (Avicel-PH-112) and magnesium stearate (Ligamed), is found to be chemically stable with rapid dissolution and bioequivalent to the marketed/reference product (VRAYLAR®).

Based on the study, it can be concluded that the above commercially viable formulations maintain the stability and exhibits desired bioavailability of the drug product. A number of other embodiments of the invention have been described. Nevertheless, it will be understood that various modifications may be made without departing from the spirit and scope of the invention. Accordingly, other embodiments are within the scope of the following claims.

We claim:

1. A stable oral formulation comprising solid dispersion or premix comprising Cariprazine or pharmaceutically acceptable salts or solvates thereof, and at least one pharmaceutically acceptable polymer/carrier selected from a group comprising of copovidone, povidone, hypromellose, hydroxylpropyl cellulose, polyvinyl caprolactam-polyvinyl acetate-polyethylene glycol and combinations thereof, and
   at least one diluent(s) which does not require to have low water activity selected from a group comprising of microcrystalline cellulose, maltodextrin, sucrose, xylitol, dextrose, sorbitol, dextrates, lactitol, kaolin, dibasic calcium phosphate, tribasic calcium phosphate, calcium carbonate, calcium sulfate, magnesium carbonate, magnesium oxide and mixtures thereof.

2. The formulation according to claim 1, wherein the diluent(s) is in the range of about 25% w/w to about 99% w/w of the formulation.

3. The solid dispersion or premix of Cariprazine according to claim 1, wherein the ratio of Cariprazine to polymers/carriers is in a range of 1:10 to 10:1.

4. The formulation according to claim 1, further comprising a pharmaceutically acceptable excipient(s) is selected from group comprising of lubricant, glidant, disintegrant, binder and buffering agent or combinations thereof.

5. The formulation according to claim 1, wherein the formulation exhibits less than about 0.5% w/w hydrolysis degradation product (De-BOC impurity) after exposure to accelerated storage conditions for about 6 months.

6. The formulation according to claim 1, wherein the formulation upon a single dose administration provides an in vivo plasma profile that is bioequivalent to currently marketed Cariprazine capsules.

7. A stable oral formulation comprising solid dispersion or premix of Cariprazine hydrochloride and copovidone (1:1 w/w), microcrystalline cellulose, and magnesium stearate.

8. A process for the preparation of stable oral pharmaceutical formulation, wherein the process comprises of the following steps:
   i) co-sift Cariprazine with excipients through sieve and mix for appropriate time in blender,
   ii) lubricate the blend with lubricant in blender and
   iii) fill the blend into capsules or compress the blend to form a tablet.

9. A method of treatment of schizophrenia, bipolar disorder, acute mania and depression in a patient, comprising orally administering to the patient a therapeutically effective amount of a stable oral formulation of Cariprazine according to claim 1.

* * * * *